(12) United States Patent
Vora et al.

(10) Patent No.: US 10,830,756 B2
(45) Date of Patent: Nov. 10, 2020

(54) METHOD TO CREATE A FREE-STANDING MEMBRANE FOR BIOLOGICAL APPLICATIONS

(71) Applicant: Applied Materials, Inc., Santa Clara, CA (US)

(72) Inventors: Ankit Vora, Bothell, WA (US); Kenichi Ohno, Sunnyvale, CA (US); Philip Allan Kraus, San Jose, CA (US); Zohreh Hesabi, San Jose, CA (US); Joseph R. Johnson, Redwood City, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 227 days.

(21) Appl. No.: 16/122,171

(22) Filed: Sep. 5, 2018

(65) Prior Publication Data

US 2019/0094203 A1 Mar. 28, 2019

Related U.S. Application Data

(60) Provisional application No. 62/561,976, filed on Sep. 22, 2017.

(51) Int. Cl.
*G01N 27/447* (2006.01)
*G01N 33/487* (2006.01)
(Continued)

(52) U.S. Cl.
CPC ... *G01N 33/48721* (2013.01); *B81C 1/00087* (2013.01); *B82B 1/002* (2013.01);
(Continued)

(58) Field of Classification Search
None
See application file for complete search history.

(56) References Cited

U.S. PATENT DOCUMENTS

2012/0021204 A1 1/2012 Pei et al.
2012/0037591 A1 2/2012 Tringe et al.
(Continued)

FOREIGN PATENT DOCUMENTS

WO 201605687 A1 4/2016

OTHER PUBLICATIONS

International Search Report and Written Opinion for Application No. PCT/US2018/050383.
(Continued)

*Primary Examiner* — J. Christopher Ball
(74) *Attorney, Agent, or Firm* — Patterson + Sheridan LLP

(57) ABSTRACT

Methods of manufacturing well-controlled nanopores using directed self-assembly and methods of manufacturing free-standing membranes using selective etching are disclosed. In one aspect, one or more nanopores are formed by directed self-assembly with block co-polymers to shrink the critical dimension of a feature which is then transferred to a thin film. In another aspect, a method includes providing a substrate having a thin film over a highly etchable layer thereof, forming one or more nanopores through the thin film over the highly etchable layer, for example, by a pore diameter reduction process, and then selectively removing a portion of the highly etchable layer under the one or more nanopores to form a thin, free-standing membrane.

9 Claims, 4 Drawing Sheets

(51) Int. Cl.
  *B82B 3/00*  (2006.01)
  *B82B 1/00*  (2006.01)
  *B81C 1/00*  (2006.01)

(52) U.S. Cl.
  CPC ..... *B82B 3/0023* (2013.01); *G01N 27/44791* (2013.01); *B81B 2203/0127* (2013.01)

(56) References Cited

U.S. PATENT DOCUMENTS

| | | |
|---|---|---|
| 2014/0262820 A1 | 9/2014 | Kuan et al. |
| 2015/0108008 A1 | 4/2015 | Kwok et al. |
| 2015/0243514 A1 | 8/2015 | Ruiz et al. |
| 2016/0042971 A1 | 2/2016 | Mohanty |

OTHER PUBLICATIONS

Liu, Zewen, et al., "Solid-State Nanopore-Based DNA Sequencing Technology", Journal of Nanomaterials, May 2016, pp. 1-13.

Yanagi, Itaru, et al.,"Fabrication of 3-nm-thick Si3N4 membranes for solid-state nanopores using the poly-Si sacrificial layer process", Scientific Reports, Oct. 2015, pp. 1-13.

Archer, Marie J., et al., "Fabrication and Characterization of Silicon Micro-Funnels and Tapered Micro-Channels for Stochastic Sensing Applications", Sensors, Jun. 2008, pp. 3848-3872.

Gadgil, V. J., et al., "Fabrication of nano structures in thin membranes with focused ion beam technology", Surface & Coatings Technology, Mar. 2009, pp. 2436-2441.

Kwok, Harold, et al., "Nanopore Fabrication by Controlled Dielectric Breakdown", Plos One, Mar. 2014, pp. 1-6.

Venkatesan, Bala Murali, et al., "Highly Sensitive, Mechanically Stable Nanopore Sensors for DNA Analysis", Advanced Materials, Jul. 2009, pp. 2771-2776.

Schneider, Grégory F., et al., "DNA translocation through Graphene Nanopore", Kavli Institute of Nanoscience, 2010, pp. 3163-3167.

Goto, Yusuke, et al., "Integrated solid-state nanopore platform for nanopore fabrication via dielectric breakdown, DNA-speed deceleration and noise reduction", Scientific Reports, Aug. 2016, pp. 1-8.

Dela Torre, Ruby, et al., "Fabrication and characterization of solid-state nanopore arrays for high-throughput DNA sequencing", Nanotechnology, Sep. 2012, pp. 1-6.

Zeng, Shuangshuang et al., "Rectification of protein translocation in truncated pyramidal nanopores", Nature Nanotechnology, Oct. 2019, pp. 1056-1062.

METHOD TO CREATE A FREE-STANDING MEMBRANE FOR BIOLOGICAL APPLICATIONS

CROSS-REFERENCE TO RELATED APPLICATIONS

This application claims benefit of U.S. Provisional Patent Application Ser. No. 62/561,976, filed on Sep. 22, 2017, which is herein incorporated by reference in its entirety.

BACKGROUND

Field

Aspects disclosed herein relate to methods of manufacturing well-controlled nanopores using directed self assembly and methods of manufacturing free-standing membranes using selective etching.

Description of the Related Art

Nanopores are widely used for applications such as deoxyribonucleic acid (DNA) and ribonucleic acid (RNA) sequencing. In one example, nanopore sequencing is performed using an electrical detection method, which generally includes transporting an unknown sample through the nanopore, which is immersed in a conducting fluid, and applying electric potential across the nanopore. Electric current resulting from the conduction of ions through the nanopore is measured. The magnitude of the electric current density across a nanopore surface depends on the nanopore dimensions and the composition of the sample, such as DNA or RNA, which is occupying the nanopore at the time. Different nucleotides cause characteristic changes in electric current density across nanopore surfaces. These electric current changes are measured and used to sequence the DNA or RNA sample.

Various methods have been used for biological sequencing. Sequencing by synthesis, or second generation sequencing, is used to identify which bases have attached to a single strand of DNA. Third generation sequencing, which generally includes threading an entire DNA strand through a single pore, is used to directly read the DNA. Some sequencing methods require the DNA or RNA sample to be cut up and then reassembled. Additionally, some sequencing methods use biological membranes and biological pores, which have shelf lives and must be kept cold prior to use.

Solid-state nanopores, which are nanometer-sized pores formed on a free-standing membrane such as silicon nitride or silicon oxide, have recently been used for sequencing. Current solid-state nanopore fabrication methods, such as using a tunneling electron microscope, focused ion beam, or electron beam, however, cannot easily and cheaply achieve the size and position control requirements necessary for manufacturing arrays of nanopores. Additionally, current nanopore fabrication methods are time consuming. Moreover, current free-standing membrane fabrication methods are manual, time consuming and costly, and cannot be efficiently used to repetitively form a free-standing membrane with the optimum thinness for DNA or RNA sequencing.

Therefore, there is a need in the art for improved methods of manufacturing well-controlled nanopores and free-standing membranes for biological applications.

SUMMARY

Methods of manufacturing well-controlled nanopores using directed self-assembly and methods of manufacturing free-standing membranes using selective etching are disclosed. In one aspect, one or more nanopores are formed by directed self-assembly with block co-polymers to shrink the critical dimension of a feature which is then transferred to a thin film. In another aspect, a method includes providing a substrate having a thin film over a highly etchable layer thereof, forming one or more nanopores through the thin film over the highly etchable layer, for example, by a pore diameter reduction process, and then selectively removing a portion of the highly etchable layer under the one or more nanopores to form a thin, free-standing membrane.

In one aspect, a method for forming a substrate is provided. The method includes providing a substrate having a thin film over a highly etchable layer thereof, forming one or more nanopores through the thin film over the highly etchable layer, and selectively removing a portion of the highly etchable layer under the one or more nanopores to form a thin, free-standing membrane.

In another aspect, a method for forming a substrate is provided. The method includes providing a substrate having a thin film over a highly etchable layer thereof, forming one or more nanopores through the thin film over the highly etchable layer, the forming the one or more nanopores including forming at least one first feature in the thin film, depositing a block co-polymer in the first feature, the block co-polymer comprising at least a first domain and a second domain, and etching the second domain, and selectively removing a portion of the highly etchable layer under the one or more nanopores to form a thin, free-standing membrane.

In yet another aspect, a substrate is disclosed. The substrate includes a first silicon layer, a dielectric layer disposed over the first silicon layer, a second silicon layer disposed over a portion of the dielectric layer, a free-standing membrane disposed over the second silicon layer, the free-standing membrane having at least one nanopore and at least one opening formed therethrough, a first well disposed below the at least one nanopore; and a second well disposed above the at least one nanopore.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of its scope, and may admit to other equally effective aspects.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

Methods of manufacturing well-controlled nanopores using directed self-assembly and methods of manufacturing free-standing membranes using selective etching are disclosed. In one aspect, one or more nanopores are formed by directed self-assembly with block co-polymers to shrink the critical dimension of a feature which is then transferred to a thin film. In another aspect, a method includes providing a substrate having a thin film over a highly etchable layer thereof, forming one or more nanopores through the thin film over the highly etchable layer, for example, by a pore diameter reduction process, and then selectively removing a portion of the highly etchable layer under the one or more nanopores to form a thin, free-standing membrane.

Methods described herein refer to formation of nanopores on a semiconductor substrate as an example. It is also contemplated that the described methods are useful to form other pore-like structures on various materials, including solid-state and biological materials. Methods described herein refer to formation of one or more trenches or tubes as examples; however, other etched features and any combinations thereof are also contemplated. For illustrative purposes a silicon on insulator (SOI) substrate with a silicon oxide layer is described; however, any suitable substrate materials and dielectric materials are also contemplated. Additionally, methods described herein refer to a topside and a backside of the substrate. The topside and backside generally refer to opposite sides of the substrate and do not necessarily refer to an upward or downward orientation.

Figure 1:
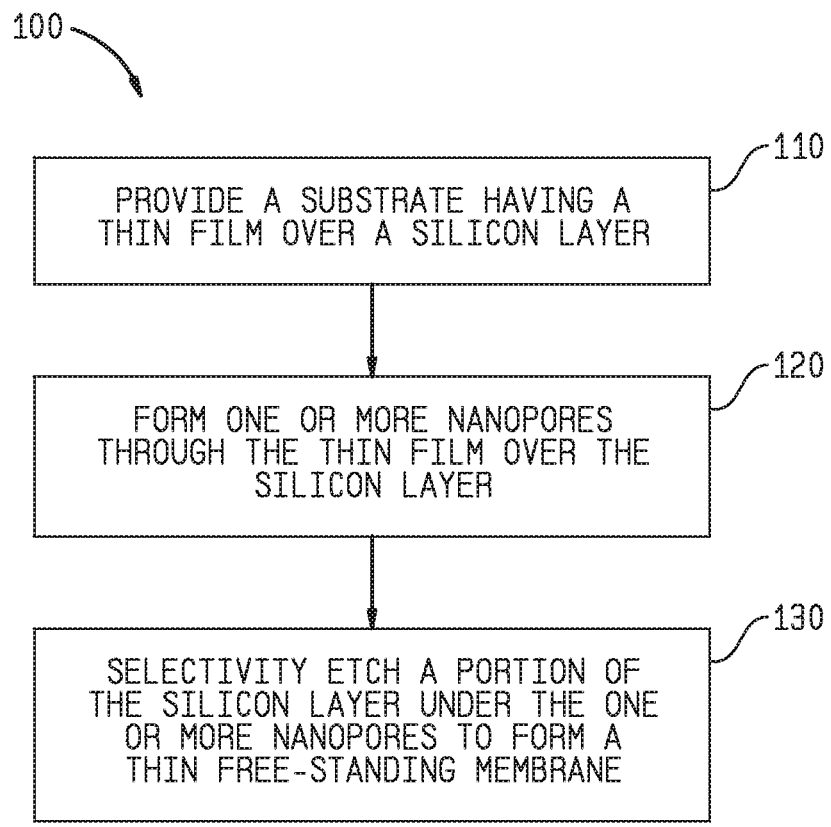
FIG. 1 is a process flow of a method for forming a substrate having a free-standing membrane for biological applications.

FIG. 1 is a process flow of a method 100 for forming a substrate having a free-standing membrane for biological applications.

Prior to method 100, a substrate is processed. A thin film is deposited over a silicon layer of the substrate. The method 100 begins at operation 110 by providing the substrate having the thin film over the silicon layer. At operation 120, one or more nanopores are formed through the thin film over the silicon layer. At operation 130, a portion of the silicon layer under the one or more nanopores is selectively etched to form a thin free-standing membrane.

The substrate is generally any suitable substrate, such as a doped or an undoped silicon (Si) substrate. The thin film deposited over the topside of the substrate is generally any suitable thin film. The thin film is generally deposited by any suitable deposition process, including but not limited to, atomic layer deposition (ALD), physical vapor deposition (PVD), chemical vapor deposition (CVD), and electron beam deposition (EBD), and is of any suitable thickness, for example less than about 10 nanometers (nm), less than about 5 nm, less than about 2 nm, or less than about 1 nm. The one or more nanopores are generally formed by any suitable technique. In the description of FIGS. 2A-2K that follows, the one or more nanopores are formed using directed self-assembly of block co-polymers as an example. It is also contemplated that the one or more nanopores are formed by other suitable methods, including but not limited to, seam exploitation, or cyclic ALD and RIE etching, and dielectric breakdown.

FIGS. 2A-2K depict cross-sectional views of a substrate 200 having a free-standing membrane with one or more nanopores therethrough according to a process flow disclosed herein, such as at various stages of the method 100.

Figure 2A:
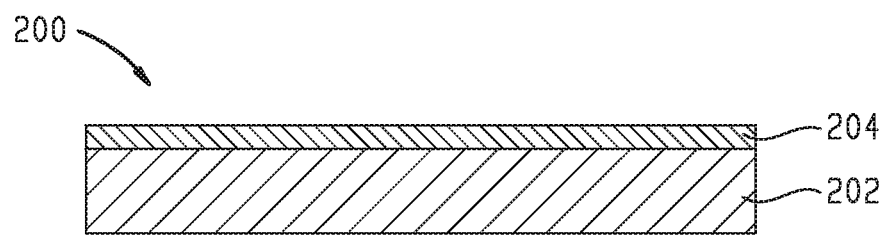
FIGS. 2A-2K depict cross-sectional views of a substrate having a free-standing membrane with one or more nanopores formed therethrough according to a process flow disclosed herein.
Figure 2B:
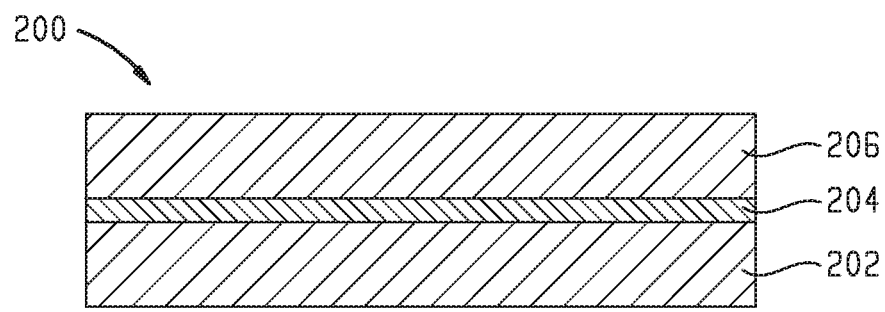

As shown in FIG. 2A, a dielectric layer, such as an oxide layer 204, is grown, formed, or otherwise deposited over a first Si layer 202. A second Si layer 206 is then deposited over the oxide layer 204 to create a silicon on insulator (SOI) substrate, as shown in FIG. 2B. A thickness of the second Si layer 206 is generally any suitable thickness, for example, between about 0.5 nm and about 200 nm, such as about 80 nm, or between about 1 micron (μm) and about 10 μm, such as about 5 μm.

Figure 2C:
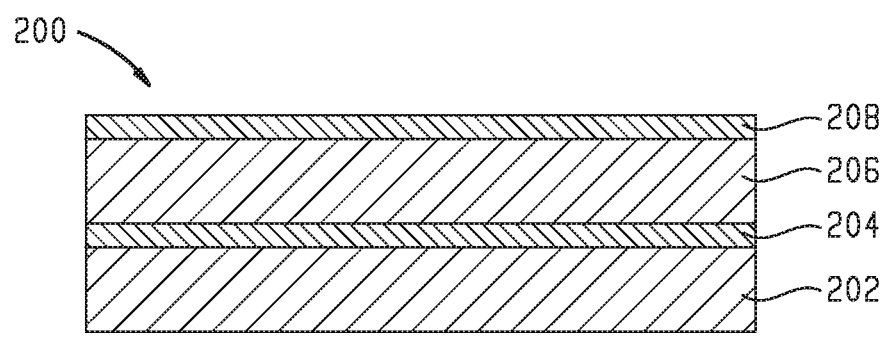

A thin film 208 is then deposited over the second Si layer 206, as shown in FIG. 2C. The thin film 208 is generally deposited by any suitable deposition process, including but not limited to ALD, and generally has a thickness less than about 60 nanometers, less than about 5 nm, less than about 2 nm, or less than about 1 nm. In the example of FIG. 2C, the thin film 208 is a silicon oxide (SiO) film.

Figure 2D:
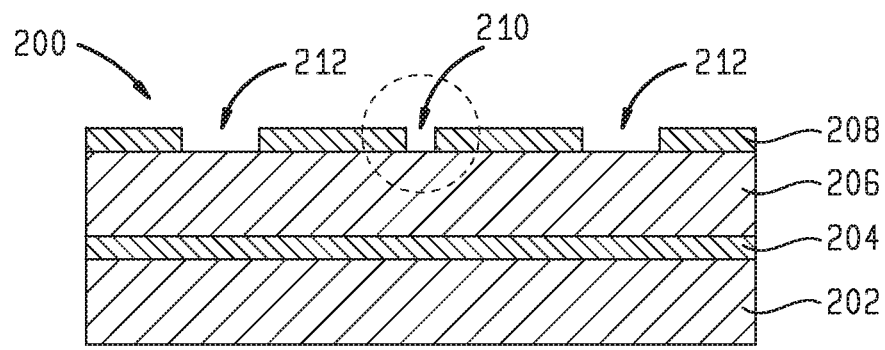
Figure 2E:
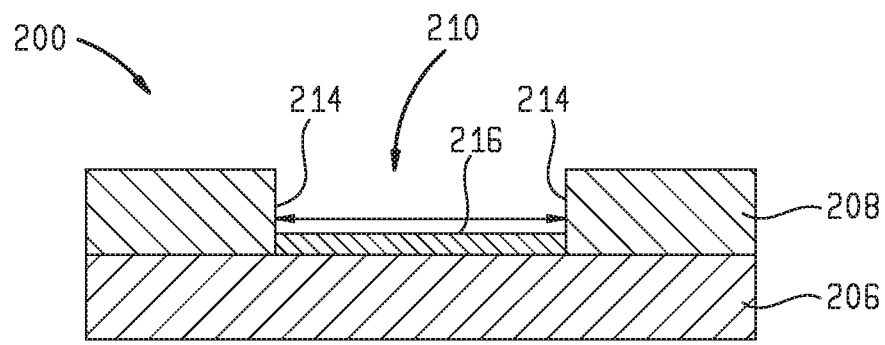

As shown in FIG. 2D, the thin film 208 is patterned with at least one first feature 210 (one is shown) and one or more second features 212 (two are shown). The patterning is generally achieved with standard lithography. In the example of FIG. 2D, the first feature 210 has a first width or diameter and the second features 212 have a second width or diameter. The first feature 210 includes one or more sidewalls 214 and a bottom 216, which corresponds to a first surface of the second Si layer 206, as shown in FIG. 2E, which is an enlarged portion of FIG. 2D. The first width or diameter is generally between about 10 nanometers (nm) and about 100 nm, for example, between about 20 nm and about 60 nm, such as about between about 35 nm and about 50 nm, such as about 50 nm. The second width or diameter is generally between about 0.5 μm and about 10 μm, such as about 1 μm.

Figure 2F:
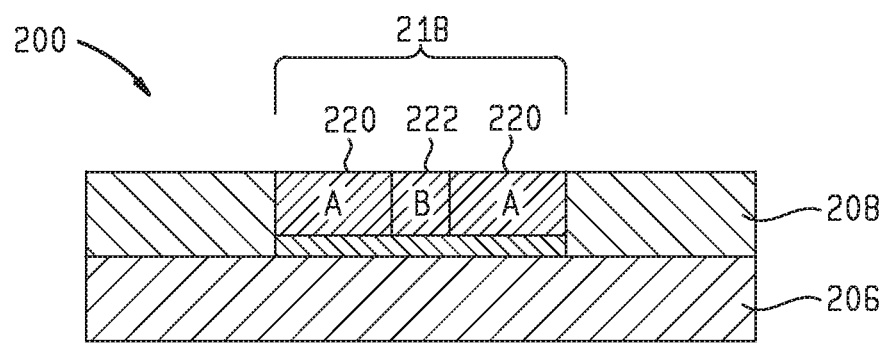
Figure 2G:
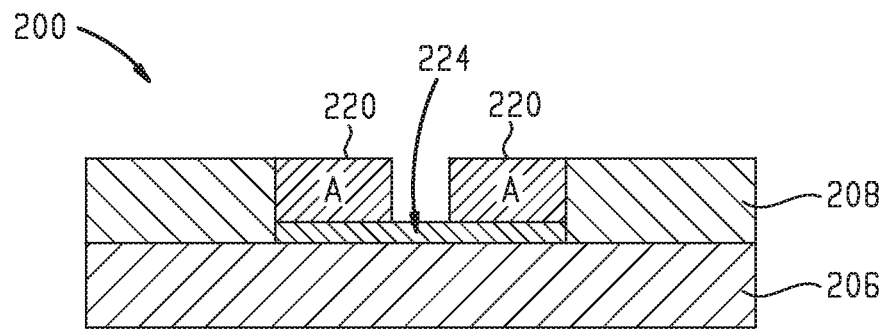
Figure 2H:
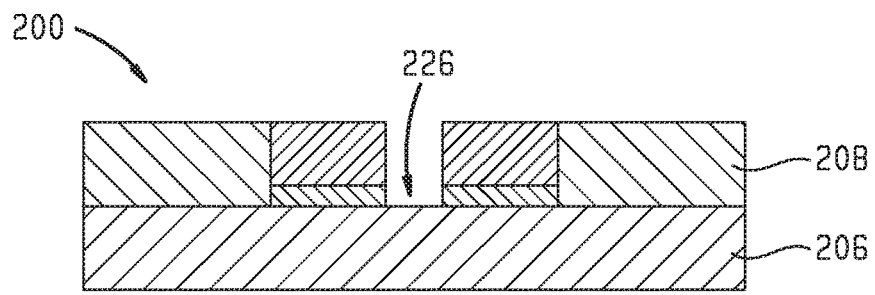
Figure 2I:
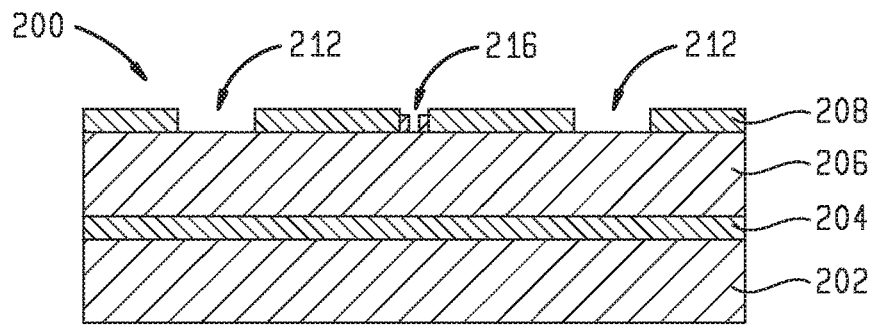

A block co-polymer 218 is deposited in the first feature 210, as shown in FIG. 2F. The block co-polymer 218 generally consists of co-polymers, which are phase separated into domains. As shown in FIG. 2F, the block co-polymer 218 is phase separated into an A domain 220 and a B domain 222. The A domain 220 is annularly around the B domain 222. The B domain 222 is generally centrally located at or near the center of the first feature 210. The B domain 222 is then selectively etched, as shown in FIG. 2G. The first feature 210 was previously etched such that there was remaining dielectric layer at the bottom of the first feature 210. The remaining block co-polymer 218 acts as a hard mask for the etching of the dielectric layer 224. Thus, a nanopore 226 is formed through the dielectric layer 224, as shown in FIG. 2H.

As discussed above, FIGS. 2A-2H illustrate an example for forming the nanopore 226 through the thin film 208. Any suitable methods for forming the nanopore 226 are also contemplated herein. For example, the nanopore may be formed by other pore diameter reduction processes, such as cyclic atomic layer deposition, or chemical vapor deposition, and etching of dielectric material, or oxidizing the substrate to form a dielectric material and breaking down the dielectric material at a weak point or seam to form a nanopore. In some aspects, one full cycle of deposition and etching will be suitable to form a well-controlled nanopore; however, in other aspects, multiple repetitions of the cycles will be suitable to form a well-controlled nanopore, depending on the size of the nanopore to be formed.

The size (i.e. diameter) of the nanopore 226 is about 100 nm or less. In one aspect, the size of the nanopore 226 is between about 1 nm and about 10 nm, for example, between about 2 nm and about 3 nm, such as about 2 nm. In another aspect, the size of the nanopore 226 is between about 0.5 nm and about 5 nm, for example between about 1 nm and about 3 nm, such as 2 nm. In another aspect, the size of the nanopore 226 is between about 1.5 nm and about 1.8 nm, such as about 1.6 nm, which is roughly the size of a single strand of DNA. In another aspect, the size of the nanopore 226 is between about 2 nm and about 3 nm, such as about 2.8 nm, which is roughly the size of double-stranded DNA.

Figure 2J:
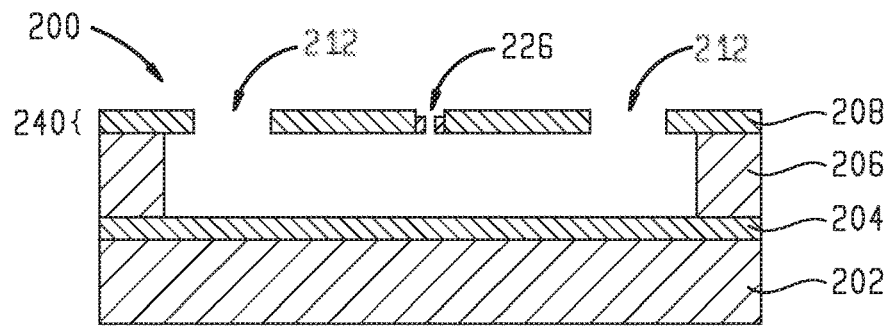
Figure 2K:
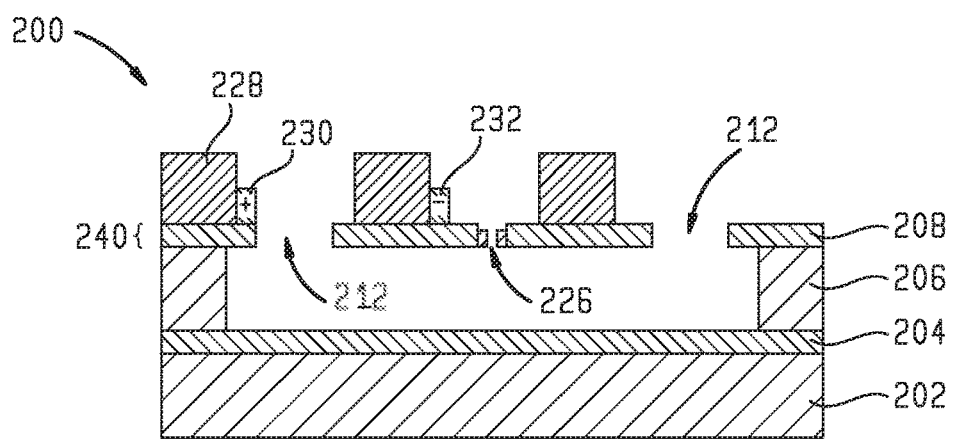

After the nanopore 226 has been formed, a selective etching process is used to remove a portion of the second Si layer 206 under the nanopore 226 and the one or more second features 212, as shown in FIG. 2J. Selectively etching the portion of the second Si layer 206 generally includes positioning the substrate 200 in an etch chamber, introducing an etchant selected for removing silicon, and exposing the substrate 200 to the silicon etchant to remove the portion of the second Si layer 206. For example, radical-based chemistry is used to deliver tunable selectivity for removal of the second Si layer 206 with atomic-level precision. The selected etchant and radicals selectively etch the second Si layer over the thin film 208. For example, the ratio of the selective etches of $SiO_2$:Si is about 1:2000. An example of a chamber for performing the selective etching is a Producer® Selectra™ Etch chamber available from Applied Materials, Inc. of Santa Clara, Calif.

While the foregoing example contemplates selectively etching an Si layer 206, it is contemplated that the etched layer is generally any suitable highly etchable layer.

Once the portion of the second Si layer 206 has been selectively etched, a free-standing membrane 240 is formed from the thin film 208, as shown in FIG. 2J. The free-standing membrane 240 includes at least one nanopore 226 and one or more openings where the one or more second features 212 were formed over the second Si layer 206. The free-standing membrane 240 is thin, for example less than or equal to about 50 nanometers, such as less than about 10 nm, less than about 5 nm, less than about 2 nm, or less than about 1 nm. The free-standing membrane 240 is any suitable material, such as a thin dielectric film.

Further substrate processing is optionally performed during the disclosed methods for forming the free-standing membrane 240. For example, an additional layer 228, such as a silicon nitride (SiN) layer, is formed over one or more portions of the free-standing membrane 240. Additionally, a positive electrode 230 and a negative electrode 232 are deposited on one or more portions of the free-standing membrane 240, thus forming a semiconductor substrate suitable for biological applications such as DNA sequencing. In the example of DNA sequencing, a first well is formed on one side of the free-standing membrane 240 and a second well is formed on the other side of the free-standing membrane 240. In one aspect, a solution having DNA therein is disposed in the first well and a solution without DNA is disposed in the second well. Since DNA is negatively charged, the DNA will follow the current and move from the first well to the second well through the nanopore 226. As the DNA moves through the nanopore 226, it will block the current going through the nanopore 226, and the change in electrical current is measured such that the DNA can be sequenced, for example, by identifying the base moving through the nanopore 226. In another aspect, a solution having DNA therein is additionally or alternatively disposed in the second well.

FIGS. 2A-2K depict various stages of a process flow according to one sequence of operations, as an example. It is contemplated that the operations shown in FIGS. 2A-2K and described herein may be performed in any suitable order. For example, in further embodiments, a portion of the second Si layer 206 may be selectively etched while the nanopore 226 is protected, and then the nanopore 226 may be unprotected while the selective etch is completed.

Benefits of the present disclosure include the ability to quickly form well-controlled nanopores and nanopore arrays, which are generally individually addressable. Disclosed methods generally provide nanopores that are well-controlled in size and in position through a thin membrane. Methods of manufacturing nanopores of well-controlled size provide improved signal-to-noise ratios because the size of the nanopore is similar to the size of the sample, such as a single strand of DNA, being transmitted through the nanopore, which increases the change in electric current passing through the nanopore. Additionally, methods of manufacturing nanopores having well-controlled positions enables a sample, such as DNA, to freely pass through the nanopore.

Methods described herein also provide free-standing membranes for biological applications, such as DNA sequencing, that are thin, for example, less than or equal to 1 nm, dielectric, chemically resistant to saline solutions (KCl), have high selectivity to chemistry of etch processes, are physically and electrically pinhole free, have low stress, and are wettable. The thinner the free-standing membrane, the more electrical field will concentrate around the edge of the nanopore, thus, the thinness of the free-standing membranes fabricated according to methods described herein allows for high signal-to-noise ratio during use for biological applications, such as DNA base identification.

While the foregoing is directed to aspects of the present disclosure, other and further aspects of the disclosure may be devised without departing from the basic scope thereof, and the scope thereof is determined by the claims that follow.

What is claimed is:

1. A method for forming a substrate, comprising:
  providing a substrate having a thin film over a highly etchable layer thereof;
  forming one or more nanopores through the thin film over the highly etchable layer using a pore diameter reduction process; and
  selectively removing a portion of the highly etchable layer under the one or more nanopores to form a thin, free-standing membrane, wherein the pore diameter reduction process comprises:
  forming at least one first feature in the thin film;
  depositing a block co-polymer in the first feature, the block co-polymer comprising at least a first domain and a second domain; and
  etching the second domain.

2. A method for forming a substrate, comprising:
  providing a substrate having a thin film over a highly etchable layer thereof;
  forming one or more nanopores through the thin film over the highly etchable layer using a pore diameter reduction process; and
  selectively removing a portion of the highly etchable layer under the one or more nanopores to form a thin, free-standing membrane, wherein the pore diameter reduction process comprises:
  forming at least one first feature in the thin film;
  depositing a dielectric material over the at least one first feature; and
  etching a portion of the dielectric material over the at least one first feature.

3. The method of claim 2, wherein the method further comprises:
  repeating the depositing the dielectric material and the etching the portion of the dielectric material until at least one nanopore is formed.

4. A method for forming a substrate, comprising:
  providing a substrate having a thin film over a highly etchable layer thereof;
  forming one or more nanopores through the thin film over the highly etchable layer using a pore diameter reduction process; and selectively removing a portion of the highly etchable layer under the one or more nanopores to form a thin, free-standing membrane, wherein the pore diameter reduction process comprises:

forming at least one first feature in the thin film;

oxidizing the substrate to form a dielectric material over the substrate to fill the at least one opening, the dielectric material having at least one seam formed therein; and exploiting the at least one seam to form at least one nanopore.

5. A method for forming a substrate, comprising:

providing a substrate having a thin film over a highly etchable layer thereof;

forming one or more nanopores through the thin film over the highly etchable layer using a pore diameter reduction process;

selectively removing a portion of the highly etchable layer under the one or more nanopores to form a thin, free-standing membrane;

depositing one or more additional layers over the thin film; and depositing a positive electrode and a negative electrode over the thin film.

6. A substrate, comprising:

a first silicon layer;

a dielectric layer disposed over the first silicon layer;

a second silicon layer disposed over a portion of the dielectric layer;

a free-standing membrane disposed over the second silicon layer, the free-standing membrane having at least one nanopore and at least one opening formed therethrough;

a first well disposed below the at least one nanopore; and a second well disposed above the at least one nanopore.

7. The substrate of claim 6, comprising:

a DNA-containing fluid in at least one of the first well and the second well.

8. The substrate of claim 6, wherein a diameter of each of the at least one nanopore is less than or equal to about 100 nanometers.

9. The substrate of claim 6, wherein a thickness of the free-standing membrane is less than or equal to about 50 nanometers.

* * * * *